(12) United States Patent
Michelini et al.

(10) Patent No.: US 11,337,715 B2
(45) Date of Patent: May 24, 2022

(54) ENDOSCOPIC GRASPING DEVICE

(71) Applicant: UNITED STATES ENDOSCOPY GROUP, INC., Mentor, OH (US)

(72) Inventors: Joseph Michelini, Painesville, OH (US); Alexis Uspenski, Rock Creek, OH (US); Alison Streiff, Painesville, OH (US); Keith R. John, Chardon, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 0 days.

(21) Appl. No.: 15/080,867

(22) Filed: Mar. 25, 2016

(65) Prior Publication Data
US 2016/0278801 A1    Sep. 29, 2016

Related U.S. Application Data

(60) Provisional application No. 62/138,757, filed on Mar. 26, 2015.

(51) Int. Cl.
*A61B 17/29* (2006.01)
*A61B 17/22* (2006.01)

(52) U.S. Cl.
CPC ........ *A61B 17/29* (2013.01); *A61B 17/22031* (2013.01); *A61B 2017/22035* (2013.01); *A61B 2017/2926* (2013.01)

(58) Field of Classification Search
CPC ............ A61B 2017/2929; A61B 10/06; A61B 17/22031; A61B 17/29;
(Continued)

(56) References Cited

U.S. PATENT DOCUMENTS

| X689606 | 12/1901 | Burgess |
|---|---|---|
| 2,034,785 A | 3/1936 | Wappler |

(Continued)

FOREIGN PATENT DOCUMENTS

| EP | 1849422 A2 * | 10/2007 | ........... A61B 17/221 |
|---|---|---|---|
| EP | 2324773 A2 | 5/2011 | |

(Continued)

OTHER PUBLICATIONS

Gap Definition. Cambridge English Dictionary accessed Nov. 16, 2020 https://dictionary.cambridge.org/US/dictionary/english/gap (Year: 2020).*

(Continued)

*Primary Examiner* — Wade Miles
*Assistant Examiner* — Kankindi Rwego
(74) *Attorney, Agent, or Firm* — Calfee, Halter & Griswold LLP (57) ABSTRACT

The present subject matter is directed to an endoscopic grasping device for capturing objects within a human subject. The device includes a fork; and two jaws pivotally mounted about a pivot point to the fork, and movable between a predetermined closed position and a predetermined open position. Each jaw comprises front teeth near a distal end of the jaw. The front teeth of both jaws are configured to substantially mesh with each other when the jaws are in the closed position. The substantially meshed front teeth of both jaws in the closed position form a substantially hemisphere-shaped distal tip.

24 Claims, 9 Drawing Sheets

(58) Field of Classification Search
CPC .. A61B 2017/22035; A61B 2017/2926; A61B 2017/2945; A61B 17/128; A61B 17/1285
USPC ........................................................ 606/207
See application file for complete search history.

(56) References Cited

U.S. PATENT DOCUMENTS

| | | | |
|---|---|---|---|
| 2,618,268 A | 11/1952 | English | |
| 2,668,538 A | 2/1954 | Baker | |
| 2,842,132 A | 7/1958 | Soltero et al. | |
| 4,598,699 A | 7/1986 | Garren et al. | |
| D289,683 S | 5/1987 | Gilfillan | |
| 4,880,015 A * | 11/1989 | Nierman | A61B 10/06 600/564 |
| 5,170,800 A | 12/1992 | Smith et al. | |
| 5,304,203 A | 4/1994 | El-Mallawany et al. | |
| D351,653 S | 10/1994 | Koros et al. | |
| 5,354,312 A | 10/1994 | Brinkerhoff et al. | |
| 5,394,885 A | 3/1995 | Francese | |
| 5,482,054 A | 1/1996 | Slater | |
| 5,553,624 A * | 9/1996 | Francese | A61B 18/1445 600/564 |
| 5,575,805 A | 11/1996 | Li | |
| 5,636,639 A | 6/1997 | Turturro et al. | |
| 5,647,115 A | 7/1997 | Slater et al. | |
| 5,819,738 A * | 10/1998 | Slater | A61B 10/06 600/564 |
| 5,922,008 A | 7/1999 | Gimpelson | |
| 5,945,979 A | 8/1999 | Kortenbach et al. | |
| 6,077,280 A | 6/2000 | Fossum | |
| 6,129,683 A | 10/2000 | Sutton et al. | |
| 6,159,162 A | 12/2000 | Kostylev et al. | |
| 6,273,860 B1 | 8/2001 | Kostylev et al. | |
| 6,309,404 B1 | 10/2001 | Krzyzanowski | |
| 6,709,445 B2 | 3/2004 | Boebel | |
| 6,743,240 B2 * | 6/2004 | Smith | A61B 17/122 600/104 |
| 6,824,548 B2 | 11/2004 | Smith et al. | |
| 6,843,794 B2 | 1/2005 | Sixto et al. | |
| 7,070,602 B2 | 7/2006 | Smith et al. | |
| 7,090,685 B2 | 8/2006 | Kortenbach et al. | |
| 7,105,000 B2 | 9/2006 | McBrayer | |
| RE39,415 E | 11/2006 | Bales | |
| 7,182,775 B2 | 2/2007 | de Guillebon et al. | |
| 7,223,272 B2 | 5/2007 | Francese et al. | |
| D545,432 S | 6/2007 | Watanabe | |
| 7,232,445 B2 | 6/2007 | Koretenbach | |
| D575,400 S | 8/2008 | Patterson et al. | |
| 7,448,525 B2 | 11/2008 | Shelton et al. | |
| D590,944 S | 4/2009 | Watanabe | |
| D610,680 S | 2/2010 | Blocher | |
| 7,828,811 B2 | 11/2010 | Kortenbach et al. | |
| D632,788 S | 2/2011 | Thouement | |
| D634,427 S | 3/2011 | Nishimura | |
| 7,927,327 B2 | 4/2011 | Lu et al. | |
| 7,942,885 B2 | 5/2011 | Sixto et al. | |
| 7,976,552 B2 | 7/2011 | Suzuki | |
| 8,066,721 B2 | 11/2011 | Kortenbach et al. | |
| 8,070,759 B2 | 12/2011 | Stefanchik et al. | |
| 8,114,119 B2 | 2/2012 | Spivey | |
| 8,262,655 B2 | 9/2012 | Ghabrial | |
| D689,606 S | 9/2013 | John et al. | |
| 8,579,897 B2 | 11/2013 | Vakharia | |
| D710,006 S | 7/2014 | John et al. | |
| D725,265 S | 3/2015 | John et al. | |
| D758,581 S | 6/2016 | Michelini et al. | |
| 2001/0021861 A1 | 9/2001 | Boebel et al. | |
| 2002/0068945 A1 | 6/2002 | Sixto | |
| 2002/0068946 A1 | 6/2002 | Kortenbach et al. | |
| 2002/0165580 A1 | 11/2002 | Zwiefel et al. | |
| 2004/0260337 A1 * | 12/2004 | Freed | A61B 10/06 606/205 |
| 2005/0033312 A1 * | 2/2005 | Suzuki | A61B 17/1285 606/110 |
| 2005/0090838 A1 | 4/2005 | Sixto et al. | |
| 2006/0004406 A1 * | 1/2006 | Wehrstein | A61B 17/28 606/205 |
| 2006/0184198 A1 * | 8/2006 | Bales | A61B 10/06 606/205 |
| 2007/0250111 A1 | 10/2007 | Lu et al. | |
| 2008/0262539 A1 | 10/2008 | Ewers et al. | |
| 2008/0294178 A1 | 11/2008 | Kortenbach et al. | |
| 2011/0112434 A1 | 5/2011 | Ghabrial | |
| 2013/0197516 A1 | 8/2013 | Kappel et al. | |
| 2014/0216187 A1 | 8/2014 | Castro | |

FOREIGN PATENT DOCUMENTS

| | | |
|---|---|---|
| JP | S552966 A | 1/1980 |
| JP | H5-31120 A | 2/1993 |
| JP | H06237940 A | 8/1994 |
| JP | 200521587 | 1/2005 |
| JP | 2005021587 | 1/2005 |
| JP | 2006-212321 A | 8/2006 |
| JP | 2008536530 A | 9/2008 |

OTHER PUBLICATIONS

Notice of Allowance from U.S. Appl. No. 29/521,712 dated Sep. 19, 2016.
Notice of Allowance from U.S. Appl. No. 29/401,032 dated Apr. 22, 2013.
Notice of Allowance from U.S. Appl. No. 29/462,413 dated Mar. 18, 2014.
Notice of Allowance from U.S. Appl. No. 29/462,413 dated Apr. 16, 2014.
Notice of Allowance from U.S. Appl. No. 29/493,931 dated Nov. 12, 2014.
Notice of Allowance from U.S. Appl. No. 29/521,711 dated Apr. 22, 2016.
International Search Report and Written Opinion from PCT/US2016/024167 dated Jun. 23, 2016.
Extended Search Report from EP Application No. 16769753.1 dated Oct. 10, 2018.
Communication Pursuant to Article 94(3) EPC from EP 16769753.1 dated Aug. 7, 2019.
English Translation of Office Action from Japanese Application No. 2017-550629 dated Jan. 22, 2020.
English Translation of Office Action from Japanese Application No. 2017-550629 dated May 27, 2020.
Exam Report from European Application No. 16769753.1 dated Dec. 9, 2020.
English Translation of Office Action from Japanese Application No. 2020-165626 dated Jul. 30, 2021.

* cited by examiner

Fig. 26

ENDOSCOPIC GRASPING DEVICE

CROSS-REFERENCE TO RELATED APPLICATION

This application claims the benefit of and priority to U.S. Provisional Patent Application Ser. No. 62/138,757, entitled ENDOSCOPIC GRASPING DEVICE and filed Mar. 26, 2015, the entire disclosure of which is incorporated herein by reference, to the extent that it is not conflicting with the present application.

BACKGROUND

Endoscopes are well-known in the medical arts and are commonly used for numerous medical procedures. One such procedure is removing objects from the inside of a human subject, such as for example, foreign bodies, excised human tissues from the wall of the gastrointestinal tract, and previously inserted medical objects, such as stents. One conventional technique for removing objects is using a grasping tool in an endoscopic procedure.

Conventional endoscopic grasping devices have one or two jaws which pivot relative to a base. The jaw or jaws at the distal end of the device may be pivoted by a user operating a handle at a proximal end of the device and at a proximal location outside of the endoscope. The object may be held by the jaws while the endoscope, grasping device, and object are removed from the patient.

The success of the user to grasp and retain objects during the procedure is dependent on several factors, including the shape and structure of the jaws.

SUMMARY

The present application describes a tool for use with an endoscope to grasp objects in the gastrointestinal tract.

In an exemplary embodiment, the endoscopic grasping device includes a fork, a first jaw having a set of teeth, and a second jaw having a set of teeth. The first jaw and the second are mounted about a pivot point on the fork and operable between an open position and a closed position.

BRIEF DESCRIPTION OF THE DRAWINGS

Features and advantages of the general inventive concepts will become apparent from the following detailed description made with reference to the accompanying drawings.

DETAILED DESCRIPTION

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

In discussing the invention, the terms "proximal" and "distal" are often used. These terms are used to describe a position or a direction with reference to the operator of the device. For example, the proximal position or proximal direction is toward the user or operator of the tool, and the distal position or direction is away from the user or operator of the tool, i.e., position or direction toward the object which the operator is attempting to grasp and retain.

A grasping device may be required in a medical procedure for many different reasons. The device may be used to retrieve objects in the body, such as foreign bodies, excised tissues, and stents. A grasping device is frequently used during an endoscopic procedures. For example, to remove a foreign body from the gastrointestinal tract, the patient is first intubated with an endoscope. A doctor will then find the foreign body in the view of the endoscope and extend the grasping device out of the distal end of the endoscope. With the foreign body comfortably near to the distal tip of the grasping device, the doctor will open the jaws around the foreign body and then close the jaws around the foreign body. The foreign body is securely held in the grasper jaws while the entire endoscope, grasping device, and foreign body are removed from the patient.

The present invention is directed to an endoscopic grasping device for capturing objects within a human subject. An embodiment of the endoscopic grasping device includes a handle with a slider on the proximal end, two jaws that are on the distal end, and a spring sheath catheter that houses two stainless steel control wires that are used to transfer the linear motion of the slider handle to open and close the jaws.

The endoscopic grasping device includes many advantageous features. The distal tip of the device is shaped to offer increased safety and performance over conventional grasping devices. When the jaws are completely closed, the distal tip is smooth and hemisphere-shaped, so as to prohibit any damage to the gastrointestinal tract of a patient during insertion or removal of the device.

The distal tip also includes interlocking front teeth, that is to say, the front teeth of both jaws are longer than the rest of the teeth on the jaw. In this manner, the front teeth extend across the centerline of the grasping device. A "zigzag" pattern on each jaw allows the teeth to interlock and yet still cross the centerline. These longer front teeth aid in capturing soft foreign bodies (such as plastic stents) by allowing the engagement of the rear and front teeth simultaneously. When the device is closed, the front teeth of each jaw mesh completely. The surface created by the meshing jaws is flat and is normal to the pulling force to keep the foreign body secure during extraction.

As discussed, the rear teeth of each jaw are shaped differently than the front teeth. The rear teeth of each jaw extend only to the centerline, at which point contact is made with rear teeth of the opposing jaw. In other words, contact is made but the rear teeth do not mesh or interlock like the front teeth. In addition, the rear teeth are shaped differently than the front teeth. The rear teeth are angle slightly back toward the rear of the jaw and extend up to a point. A radius is not intentionally manufactured at the top of each tooth. This "point to point" back-angled shape for the rear teeth increases the pressure between the teeth for holding foreign bodies. In other words, the force per contact area is increased as compared to a dull tooth.

The jaws include another feature to increase the bite unit pressure area. Each jaw includes a so-called "cupped portion" to prevent teeth from extending from one side of the jaw to the other side of the jaw. This structure reduces the surface area that the teeth come in contact with to increase the unit pressure. In other words, a bar doesn't connect a tooth on the right side on the jaw with an equally positioned tooth on the left side of the jaw. Other known devices have full bars which extend from one side of the jaw to the other side of the jaw.

The jaw shape includes a predetermined area for capturing objects. A gap is included between the front teeth and rear teeth which allows foreign bodies (such as paperclips, safety pins, etc.) to be captured within the slot. This feature works with the flat surface created by the interlocking front teeth feature when pulling out the foreign body, as it will not pull the jaws apart.

The jaws include a structure feature to create a stronger bite. Extending in the proximal direction from the pivot point for each jaw, the tang portion of the jaw has been extended. This extension allows for more leverage and creates a stronger bite, which will hold foreign bodies better. As discussed, the tang is defined as the distance from the pivot hole to the control wire hole. For example, the tang of the discussed embodiment is approximately at least 40% longer than conventional device of this size.

As discussed, the present invention is directed to an endoscopic grasping device for capturing objects within a human subject. An embodiment of the endoscopic grasping device includes a fork, a first jaw having a set of teeth, and a second jaw having a set of teeth. The first jaw and the second jaw are mounted about a pivot point on the fork and operable between an open position and a closed position.

The endoscopic grasping device may include a body, a handle mounted to and movable relative to the body, a conduit having a first end fixed to the body and a second end remote from the body, with the conduit defining a passage, a link having a first end fixed to the handle and a second end remote from the body, the link extending through at least a portion of the conduit, a first control wire connecting the link and the first wire, and a second control wire connecting the link and the second wire. The first jaw and the second jaw may be operable between an open position and a closed position by movement of the handle.

An embodiment of the endoscopic grasping device may have advantageous features related to the distal tip. The front teeth of the first jaw and the front teeth of the second jaw may each extend across a centerline of the jaw in an interlocking pattern. Also, the first jaw and the second jaw may define a smooth distal tip in a closed position. Further, the front teeth of the first jaw and the front teeth of the second jaw may interlock in a closed position to define a hemisphere-shaped distal tip. Likewise, the distal tip of the device may be atraumatic.

In regard to the rear teeth of the endoscopic grasping device, the rear teeth of the first jaw may be contiguous with the rear teeth of the second jaw at a centerline of the jaw. Also, the rear teeth of the first jaw and the rear teeth of the second jaw each are pointed with essentially no radius.

In an embodiment of the endoscopic grasping device, the tang of the teeth is advantageously shaped. At least one of the first jaw or the second jaw may extend from the pivot point in the proximal direction at least 33% of the length of which it extends in the distal direction from the pivot point.

In regard to an object capture area, at least one of the first jaw or the second jaw may define a gap between the front teeth and the second row of teeth. Further, the gap may define an object capture area.

An embodiment of the invention will now be discussed. Referring now to the drawings, an exemplary embodiment is illustrated in FIGS. 1-16, and another exemplary embodiment is illustrated in FIGS. 17-24. The two embodiments share many of the same features, which is apparent by the drawings. Further, the individual jaws of each embodiments share many of the same features with the companion jaw on the same embodiment, and with the jaws of the other embodiment. It should be apparent to one with skill in the art other jaws having one or more different features may be used in the practice of this invention.

Figure 1:
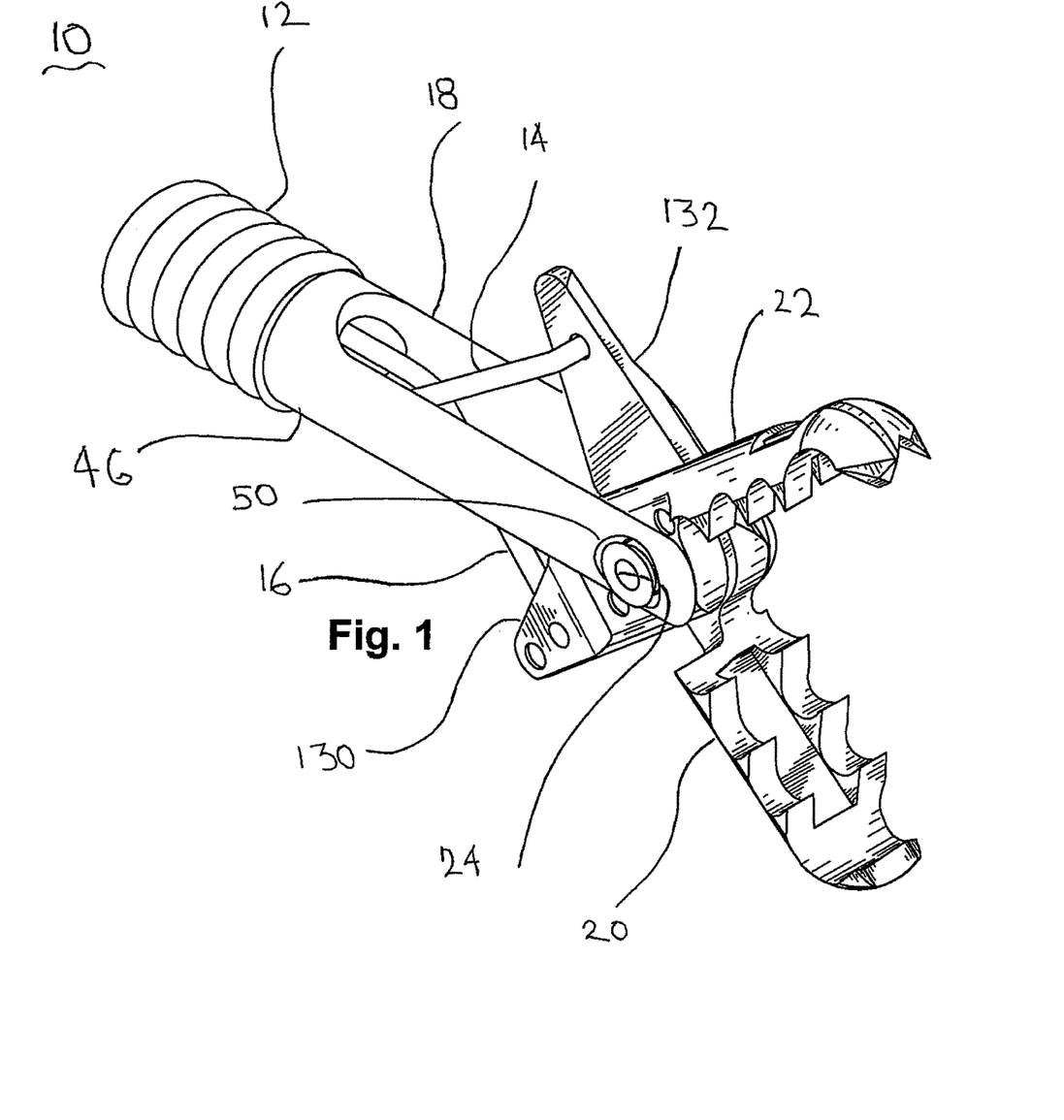
FIG. 1 is a right, side perspective view of the distal end of an endoscopic grasping device, with the jaws of the device shown in an open position.
Figures 3, 4:
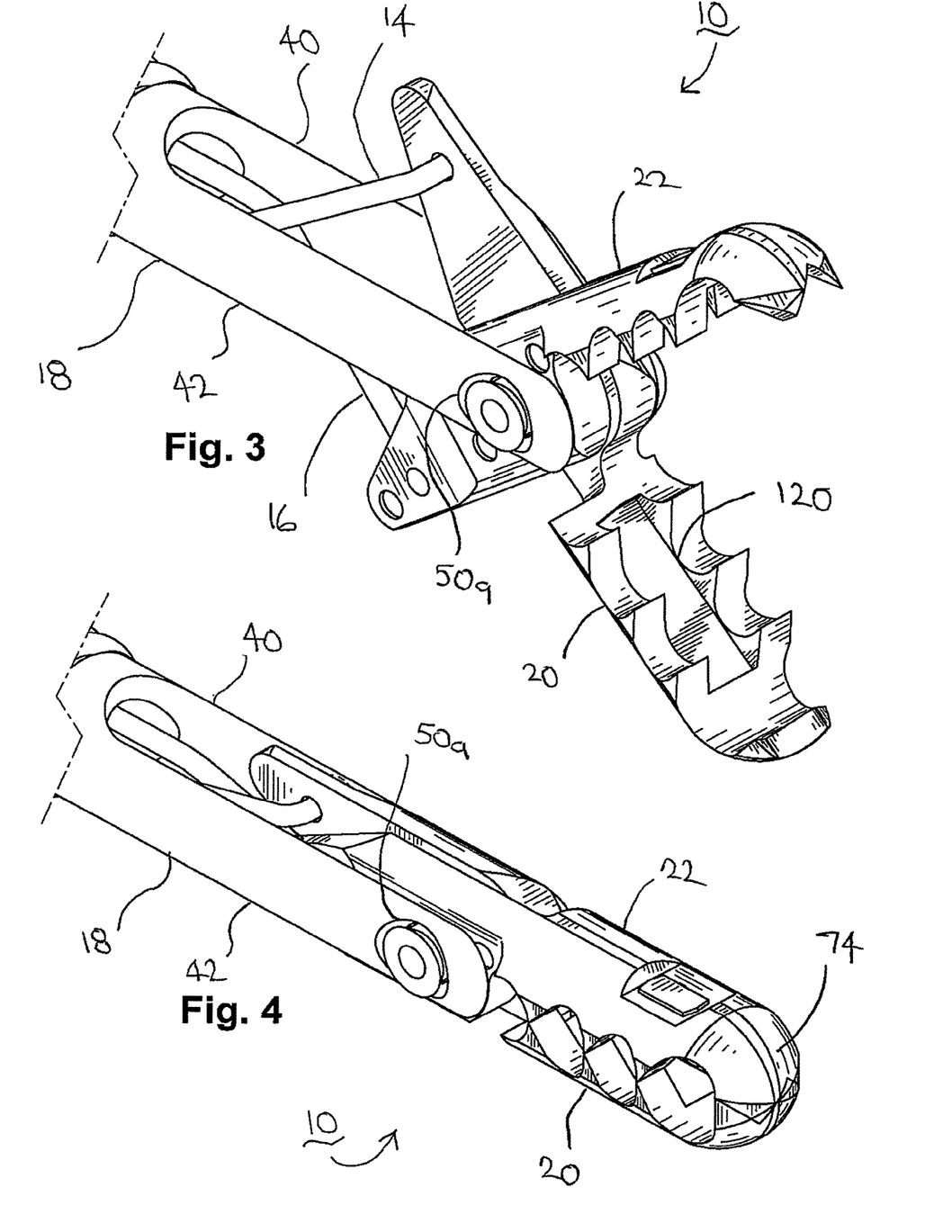
FIG. 3 is an enlarged view of FIG. 1.
FIG. 4 is a right, side perspective view of the distal end of the endoscopic grasping device of FIG. 1, with the jaws of the device shown in a closed position.

Referring now to FIG. 1, a right, side perspective view of the distal end of an endoscopic grasping device 10 is shown. The jaws are shown in an open position and in a position ready to capture a foreign object. FIG. 3 is an enlarged view of FIG. 1. The device 10 includes a spring sheath catheter 12, two control wires 14, 16, a fork 18, and two jaws 20, 22 pivotally mounted to the fork 18 by a rivet 24. The control wires 14, 16 run through the sheath toward the proximal end on the device 10. Movement of the control wires 14, 16 in the distal direction opens the jaws 20, 22 and movement of the control wires in the proximal direction closes the jaws 20, 22. Movement of the control wires 14, 16 is controlled by manipulation of the handle by a user. It should be apparent to one skilled in the art that the mechanical aspects of the catheter, link and handle may vary in the practice of this invention.

Figure 2:
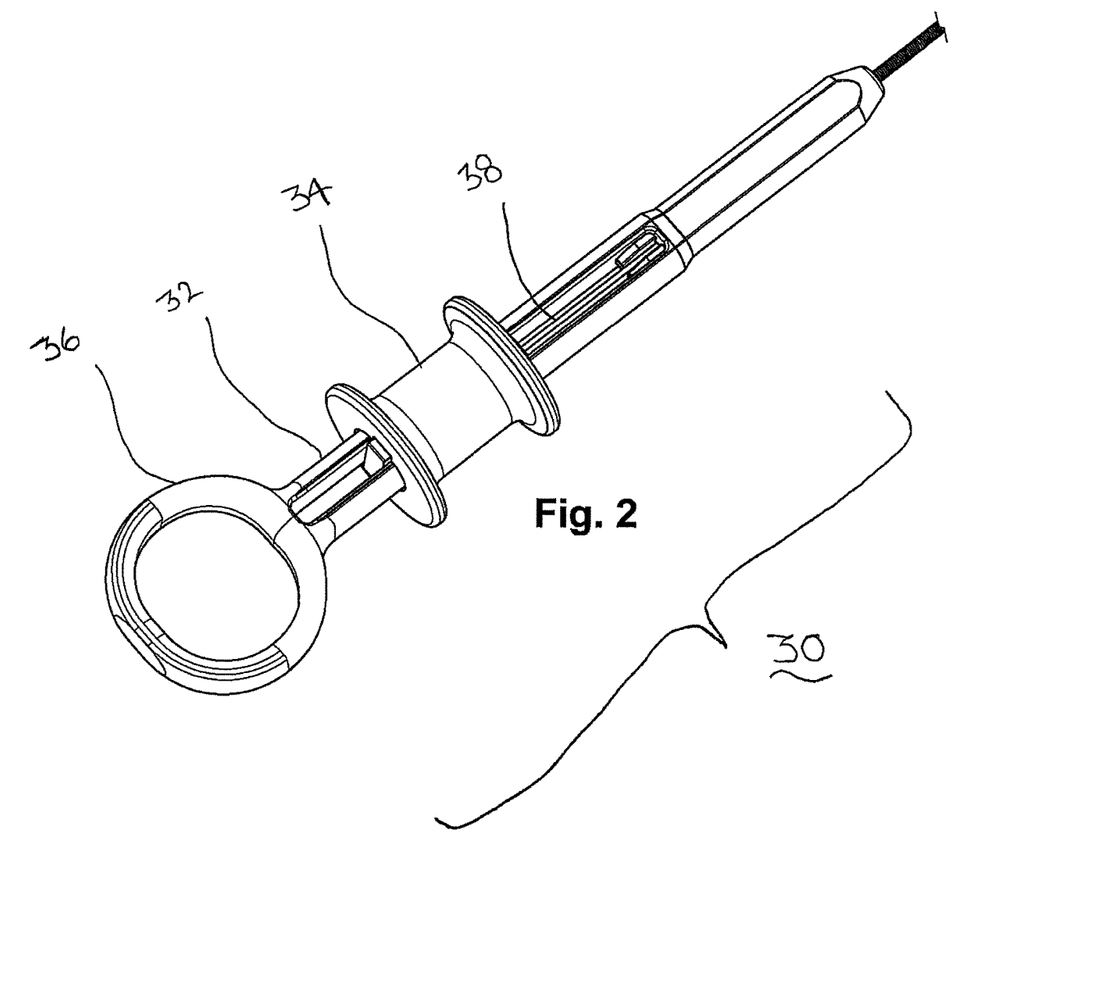
FIG. 2 is a right, side perspective view of the proximal end of the endoscopic grasping device of FIG. 1.

Referring now to FIG. 2, the proximal end of the endoscopic grasping device 10 is shown. A handle assembly 30 is shown and includes a base 32 and a slider 34. The handle is used to transfer the linear motion of the slider 34 to open and close the jaws on the distal end of the grasping device. In operation of the handle 30, a user may insert a thumb from one hand into a ring 36 and rest several fingers from the same hand on, or around the slider 34. Manual movement of the slider 34 relative to the base 32 causes movement of a link 38. The link 38 may be attached directly or indirectly to the control wires 14, 16 within the spring sheath catheter 12. Consequently, the user may open the jaws 20, 22 by actuating the slider 34 and moving it in the distal direction and close the jaws by moving the slider in the proximal direction. It should be apparent to one skilled in the art that the design and operation of the handle assembly and the link to the control wires may vary in the practice of this invention.

Referring again to FIG. 1, the spring sheath catheter 12 runs the length of the device 10 from the fork 18 to the handle 30. The spring sheath catheter 12 is formed of a coil wire and can be a variety of shapes, such as for example, a circular cross section or a rectangular cross section. The spring sheath may be PTFE (Teflon) coated or a heat shrink coated on the outside. The diameter of the spring sheath catheter 12 may vary in diameter, such as for example, the outside diameter range may be 0.080 cm to 0.100 cm. In some embodiments, The diameter of the spring sheath catheter 12 is between 0.160 cm to 0.190 cm. The length of the sheath is long enough to allow reasonable length beyond the proximal end and beyond the distal end of an endoscope, such as for example, the total working length of the device 10 may be 165 cm. In some embodiments, the total working length of the device 10 is between 165 cm to 260 cm. In some other embodiments, the total working length of the device 10 is between 165 cm to 200 cm.

Within the sheath, the two control wires run the length of the device. The control wires 14, 16 within the sheath 12 may be stainless steel, or any suitable material. The inside of the sheath may be either coated with lubricious material, such as HDPE, or have a tubing of some lubricious material, such as HDPE, running through the length of the device. The tubing reduces metal-on-metal contact between the sheath and the wires to reduce wear and provide for a smoother operation. Other friction-reducing structure may be used in the practice of this invention.

The jaws 20, 22 of the exemplary embodiment shown in FIGS. 1-16 will now be discussed. Although the discussion will focus on the upper jaw 22 as shown in FIGS. 10-16, many qualities and features of the upper jaw 22 are shared by the lower jaw 20, and statements regarding the upper jaw usually apply to the lower jaw.

The fork provides a mounting location for the jaws. As shown in FIGS. 1, 3, and 4, the fork 18 includes two tangs 40, 42 protruding distally from a base 46. Each tang defines a mounting aperture through which the rivet 24 is placed. A space between the tangs allow for pivoting movement of the jaws 20, 22 in either rotational direction.

As discussed, the endoscopic grasping device 10 includes a fork 18, a first jaw 20, and a second jaw 22. Each jaw has a set of teeth which includes front teeth and rear teeth. As seen in FIGS. 1, 3, and 4, the first jaw 20 and the second jaw 22 are mounted about a pivot point 50 on the fork 10. The jaws 20, 22 are operable between an open position, for example, as shown in FIG. 3, and a closed position, for example, as shown in FIG. 4, by movement on the slider 34 relative to the ring 36. The jaws 20, 22 may be constructed from any suitable material known in the art. For example, the jaws may be constructed from stainless steel.

The jaws 20, 22 are mounted to pivot about a pivot point 50a on each fork. As discussed, a rivet 28 is mounted through an aperture 50b on the first jaw 20 and an aperture 50c on the second jaw 22. The jaws 20, 22 include a tang 130, 132, respectively, which extend proximally from the pivot point. It should be apparent to one with skill in the art that other mounting structure may be used in the practice of this invention.

Figures 5, 6:
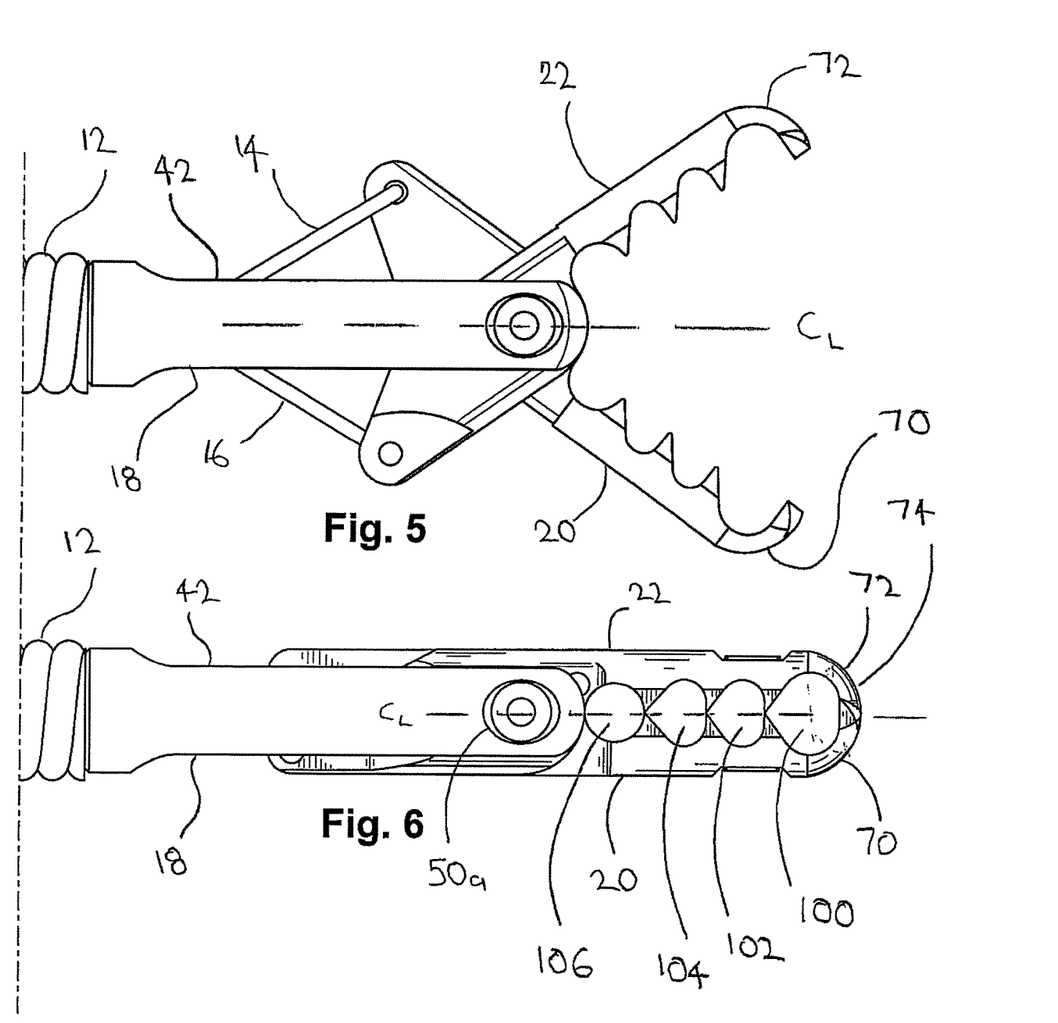
FIG. 5 is a right side view of the distal end of the endoscopic grasping device of FIG. 1, with the jaws of the device shown in an open position.
FIG. 6 is a right side view of the distal end of the endoscopic grasping device of FIG. 1, with the jaws of the device shown in a closed position.
Figure 7:
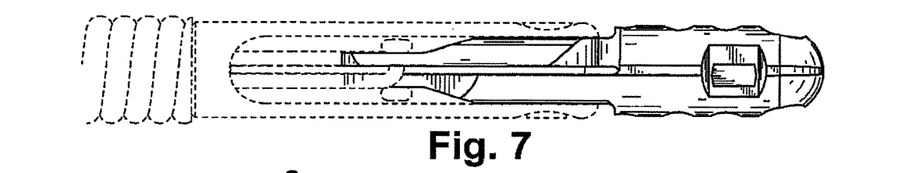
FIG. 7 is a top view of the distal end of the endoscopic grasping device of FIG. 1, with the jaws of the device shown in a closed position.

Each jaw includes several features, so as one jaw of a pair of jaws, the pair of jaws may collectively offer several benefits. As discussed, the jaws in a closed position form a smooth, atraumatic distal tip. More specifically, the front teeth of the front jaw and the front teeth of the second jaw interlock in a closed position to define a hemisphere-shaped distal tip. For example, FIG. 6 shows the grasping device 10 in a right side view in a closed position. The distal surface 70 of the first jaw, or the lower jaw 20, combines with the distal surface 72 of the second jaw, or upper jaw 22, to form a smooth tip 74. A perspective view of the distal tip is shown in FIG. 4. This hemisphere-shaped distal tip prohibits soft tissue injury during insertion and removal of the grasping device from the patient.

Figures 8, 9, 10:
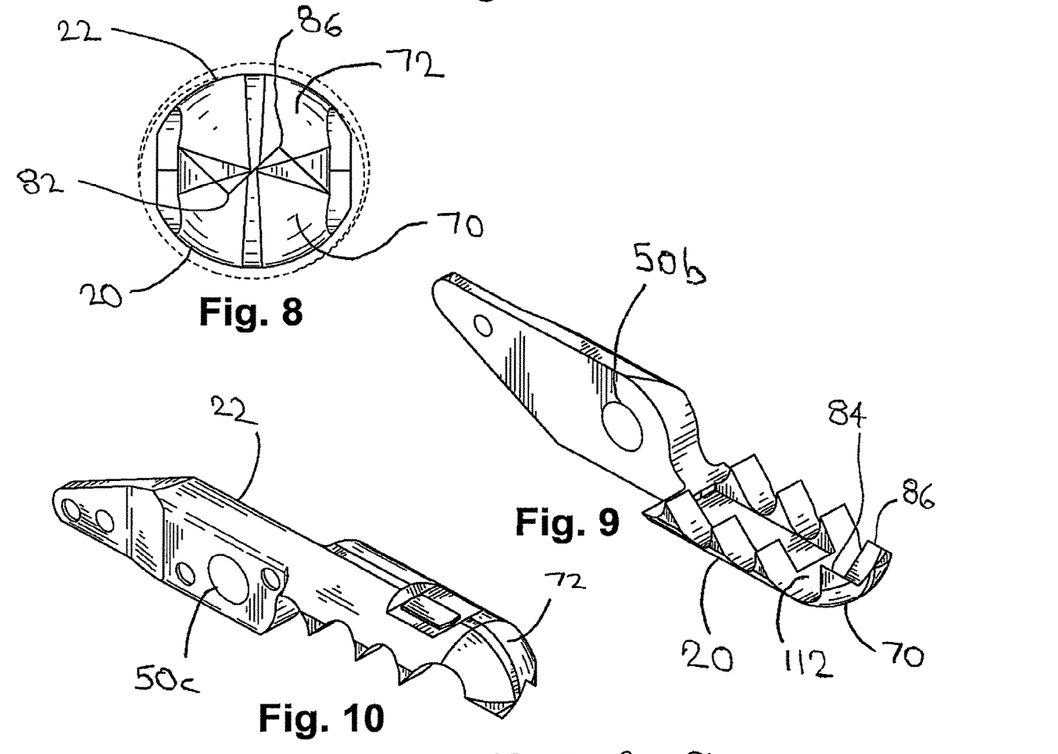
FIG. 8 is a front view of the distal end of the endoscopic grasping device of FIG. 1, with the jaws of the device shown in a closed position.
FIG. 9 is a right, top perspective view of the lower jaw of FIG. 1.
FIG. 10 is a right, top perspective view of the upper jaw of FIG. 1.
Figures 12, 13:
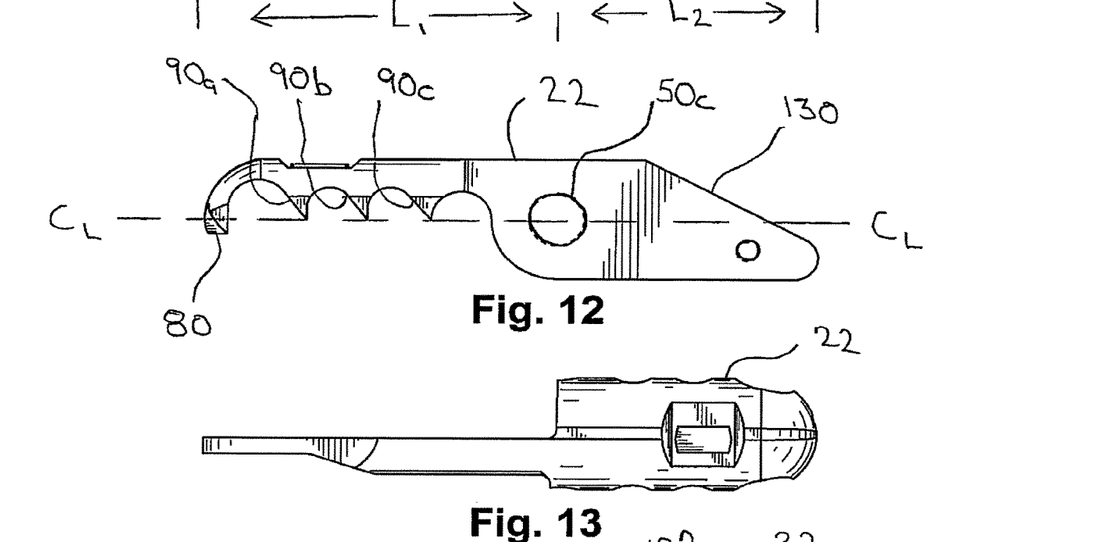
FIG. 12 is a left side view of the upper jaw of FIG. 1.
FIG. 13 is a top view of the upper jaw of FIG. 1.
Figure 15:
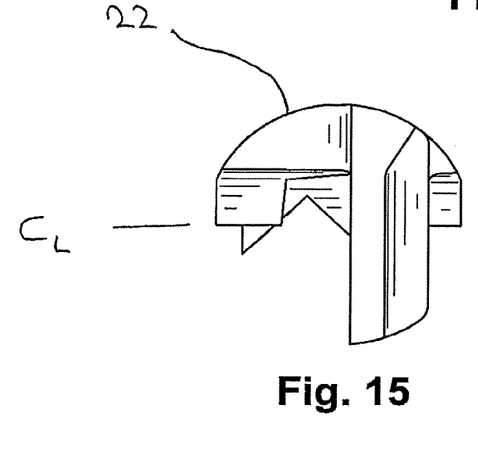
FIG. 15 is a rear view of the upper jaw of FIG. 1.
Figure 16:
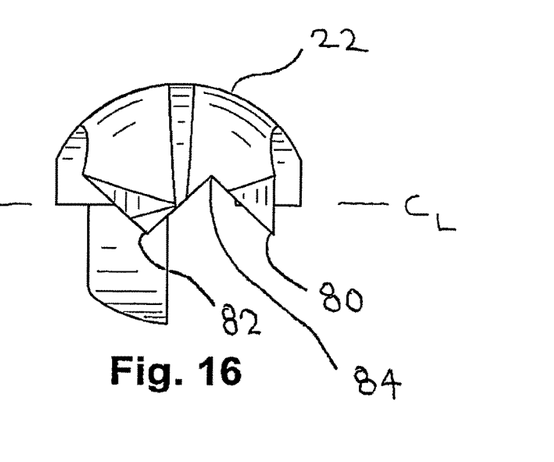
FIG. 16 is a front view of the upper jaw of FIG. 1.

The front teeth and the rear teeth extend at different lengths on each jaw. For example, the front teeth of the first jaw and the front teeth of the second jaw each extend beyond a centerline of the jaw in an interlocking pattern. For example, as shown in FIGS. 12, 15, and 16, the front teeth 80, 82 of the upper jaw 22 each extend each extend beyond a centerline $C_L$ of the upper jaw 22. As shown in FIG. 16, a gap 84 in the teeth form a "zigzag" pattern. As such, the teeth 80, 82 interlock with the front teeth 84, 86 of the lower jaw 20, as best shown in FIG. 8. The interlocking prevents any lateral movement of either jaw, and creates a flat surface to keep the jaws closed when holding a foreign object which may have a tendency to twist or turn during withdraw from the body.

Figure 11:
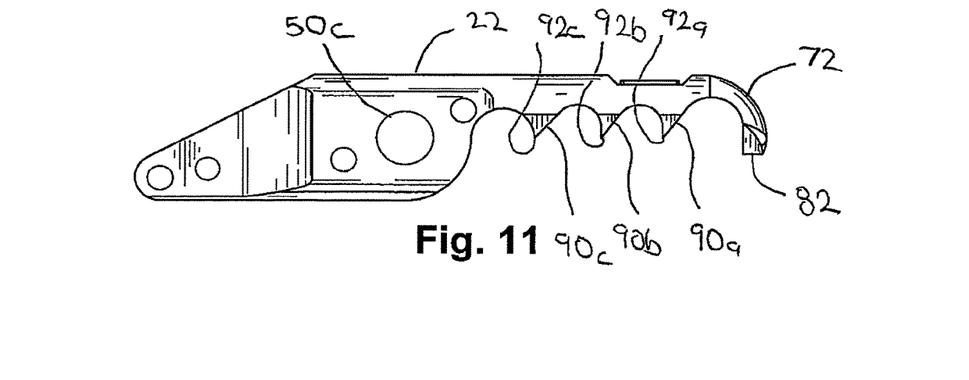
FIG. 11 is a right side view of the upper jaw of FIG. 1.

Referring to FIGS. 11 and 12, the centerline $C_L$ of the jaw is defined as the axis through the pivot point 50c. A feature of the rear teeth can be seen in this right side view and left side view. The front teeth 80 extend beyond the centerline CL and the rear teeth 90a, 90b, 90c extend to only the centerline $C_L$. The two sets of rear teeth meeting at the centerline $C_L$ are illustrated in FIG. 6. As shown, the rear teeth of the first jaw 20 are contiguous with the rear teeth 22 of the second jaw at a centerline $C_L$ of the jaw.

Further as best shown in FIG. 11, the rear teeth of each jaw are advantageously shaped. FIG. 11 is a right side view of the upper jaw 22. The upper jaw has three rows of rear teeth 90a, 90b, 90c. As clearly shown in the Figure, each rear tooth has a front profile which is back-angled, or sloping downward toward the distal tip of the jaw from a point. The upper jaw 22 is machined to form a point 92a, 92b, 92c at the top of each tooth 90a, 90b with essentially no radius. The pointed and shaped edge for the rear teeth promotes gripping onto foreign objects made of soft plastics, such as for example, stents, tubing or other types of plastics.

Figure 14:
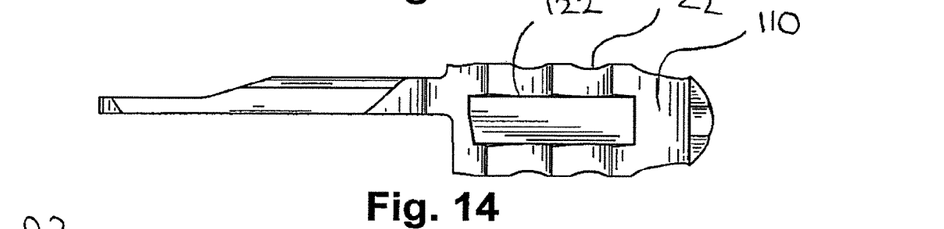
FIG. 14 is a bottom view of the upper jaw of FIG. 1.

As shown in the side view of the grasping device 10 in the closed position, the rear teeth of the two jaws 20, 22 form several open cross-sectional areas, a large tear-drop shaped area 100 near the distal tip 74, two smaller, intermediate positioned and similar shaped areas 102, 104, and a circular shaped area 106 at the rear of the teeth. Specifically, the first jaw 20 and the second jaw 22 each define a gap between the front teeth and the second row of teeth. For example, FIG. 14 is a bottom view of the upper jaw 22 of FIG. 1. A concave surface 110 runs from the front teeth to the distal most set of rear teeth. This concave surface 110, combined with a correspondingly shaped and correspondingly placed concave surface 112 on the lower jaw 20 (see FIG. 9), define a gap 100. The gap 100 may define an object capture area for the grasping device.

As discussed, the proximal end of the jaws are beneficial for increased grasping strength. The portion of the jaw extending proximally from the pivot point is known as the tang 130, as shown in FIG. 12. In the embodiment on FIGS. 11-16, the jaws have an increased tang length over the known grasping devices. The increased tang length promotes an increased grasping strength. For example, the jaw 22 extends from the pivot point 50c in the proximal direction at least 33% of the length which it extends in the distal direction from the pivot point. As applied to FIG. 12, for example, the distance $L_1$ is no greater than 3 times the length of $L_2$. In another embodiment, the distance $L_1$ is no greater than 2 times the length of $L_2$.

Figure 25:
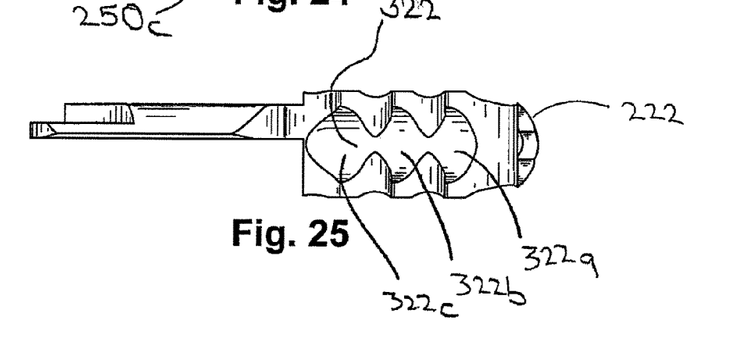
FIG. 25 is a bottom view of the upper jaw of FIG. 17.
Figure 26:
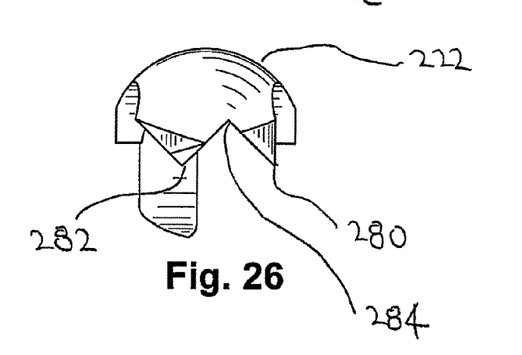
FIG. 26 is a front view of the upper jaw of FIG. 17.

Another feature of the jaws is increase the bite unit pressure area. Each jaw includes a so-called "cupped portion" to reduce the surface area that the teeth come in contact with the teeth on the opposing jaw. In other words, a bar doesn't connect a tooth on the right side on the jaw with a equally positioned tooth on the left side of the jaw. As best seen in FIGS. 3 and 14, the lower and upper jaws 20, 22 includes a elongated cupped portion 122 to separate teeth on either side of the jaw. It should be apparent to one with skill in the art that the cupped portion may be of another shape or size during the practice of this invention. For example, FIG. 25 is a bottom view of an upper jaw having a cupped portion of a different shape.

Another embodiment of the invention will now be discussed. Referring now to the drawings, another exemplary embodiment is illustrated in FIGS. 17-26. This embodiment shares many features of the previously discussed embodiment. The device 200 includes two control wires 214, 216, a fork 218, and two jaws 220, 222 pivotally mounted to the fork 218 by a rivet 224. As discussed, many features of the jaws 20, 22 on the embodiment shown in FIGS. 1-16, are shared by the jaws 220, 222 of the embodiment shown in FIGS. 17-26.

Figure 17:
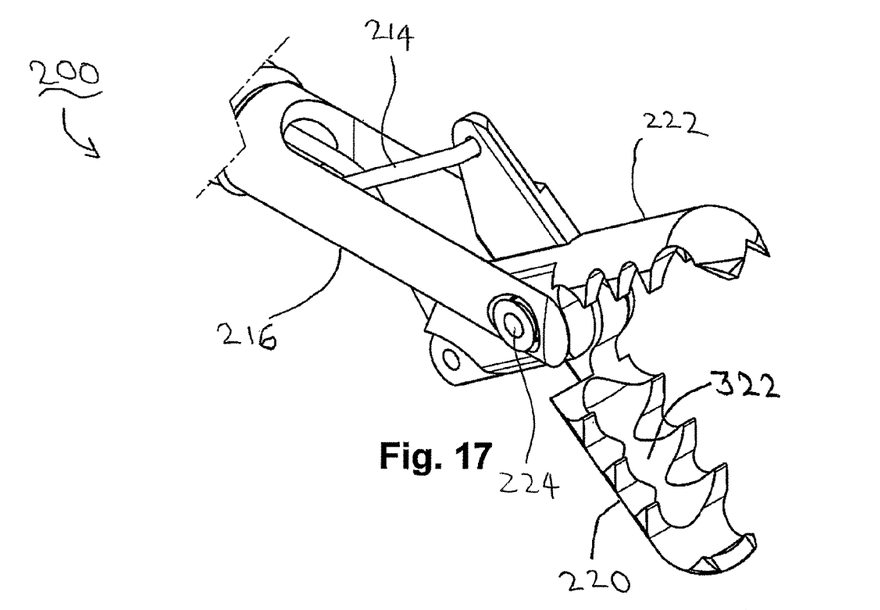
FIG. 17 is a right, side perspective view of the distal end of another endoscopic grasping device, with the jaws of the device shown in an open position.
Figure 18:
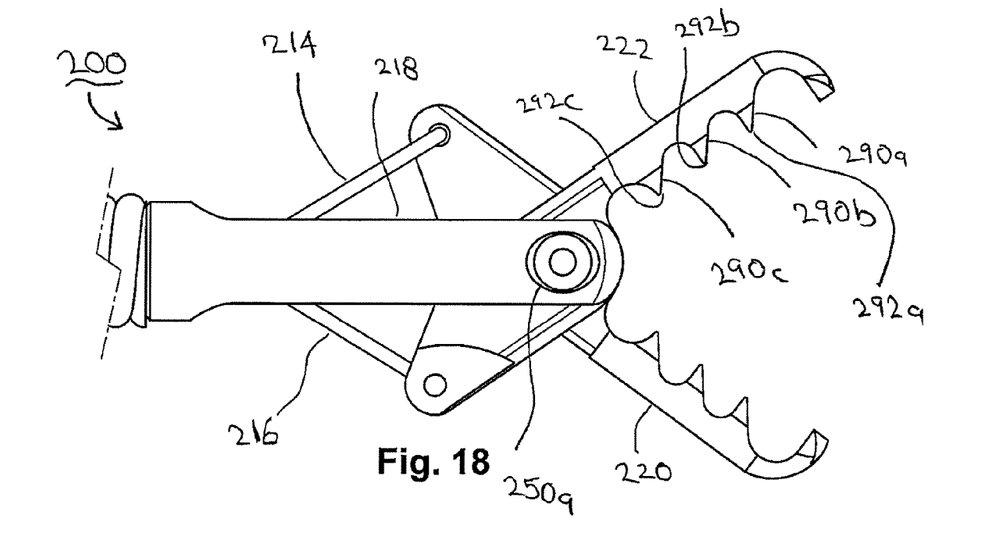
FIG. 18 is a right side view of the distal end of the endoscopic grasping device of FIG. 17, with the jaws of the device shown in an open position.

The control wires 214, 216 run through the sheath toward the proximal end on the device 10. Movement of the control wires 214, 216 in the distal direction opens the jaws 220, 222 and movement of the control wires in the proximal direction closes the jaws 220, 222. Movement of the control wires 214, 216 is controlled by manipulation of the handle by a user. The way in which the jaws are secured together, and to the fork, may be modified in the practice of this invention.

Figure 24:
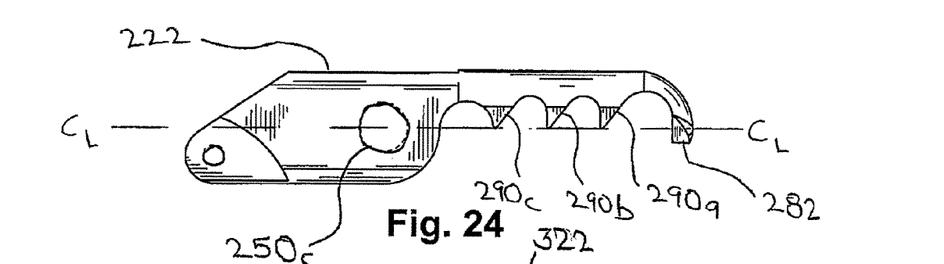
FIG. 24 is a right side view of the upper jaw of FIG. 17.

Further as best shown in FIG. 24 the rear teeth of each jaw are advantageously shaped. FIG. 24 is a right side view of the upper jaw 222. The upper jaw has three rows of rear teeth 290 a, 290 b, 290 c. Each rear tooth may include a front profile which is back-angled, and/or sloping downward toward the distal tip of the jaw from a point. The pointed and shaped edge for the rear teeth promotes gripping onto foreign objects made of soft plastics, such as for example, stents, tubing or other types of plastics.

Each jaw includes several features to collectively offer several benefits as a pair of jaws. As discussed, the jaws in a closed position for a smooth, atraumatic distal tip. More specifically, the front teeth of the front jaw and the front teeth of the second jaw interlock in a closed position to define a hemisphere-shaped distal tip. The distal surface 270 of the first jaw, or the lower jaw 220, combines with the distal surface 272 of the second jaw, or upper jaw 222, to form a smooth tip 274. This hemisphere-shaped distal tip prohibits soft tissue injury during insertion and removal of the grasping device from the patient.

Figures 22, 23:
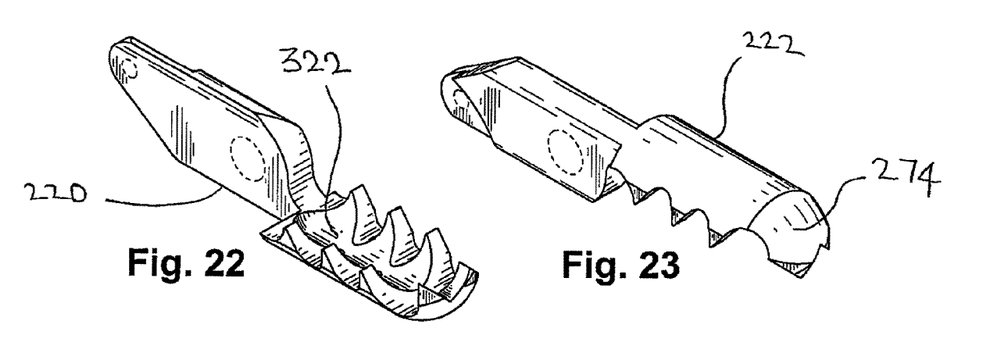
FIG. 22 is a right, top perspective view of the lower jaw of FIG. 17.
FIG. 23 is a right, top perspective view of the upper jaw of FIG. 17.

The jaws 220, 222 are shaped to increase the bite unit pressure area. Each jaw includes a so-called "cupped portion" to reduce the surface area of contact with the teeth on the opposing jaw. The cupped portion is a concave area between the right and left side of the jaw. In a conventional grasping device, a bar connects a tooth on the right side on the jaw with a equally positioned tooth on the left side of the jaw. As best seen in FIGS. 22 and 25, the lower and upper jaws 220, 222 includes a cupped portion 322 to separate teeth on either side of the jaw. The cupped portion 322 is formed by a series of shaped areas 322a, 322b, 322c. It should be apparent to one with skill in the art that the cupped portion may be of another shape or size during the practice of this invention.

Figure 19:
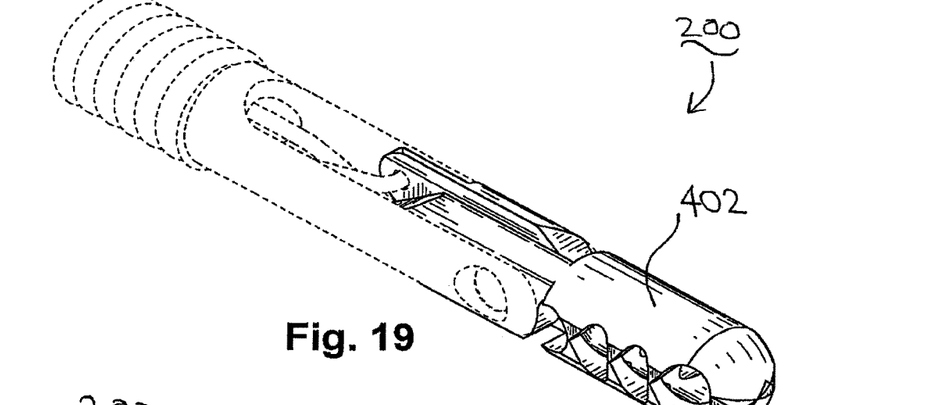
FIG. 19 is a right, side perspective view of the distal end of the endoscopic grasping device of FIG. 17, with the jaws of the device shown in a closed position.
Figure 20:
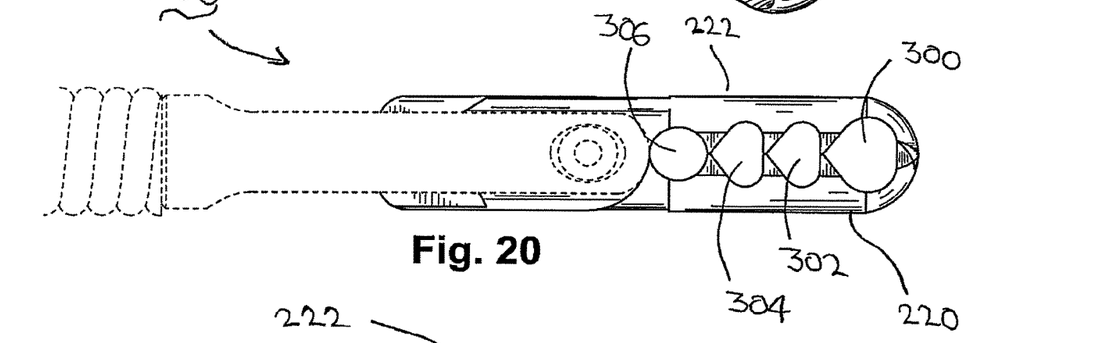
FIG. 20 is a right side view of the distal end of the endoscopic grasping device of FIG. 17, with the jaws of the device shown in a closed position.
Figure 21:
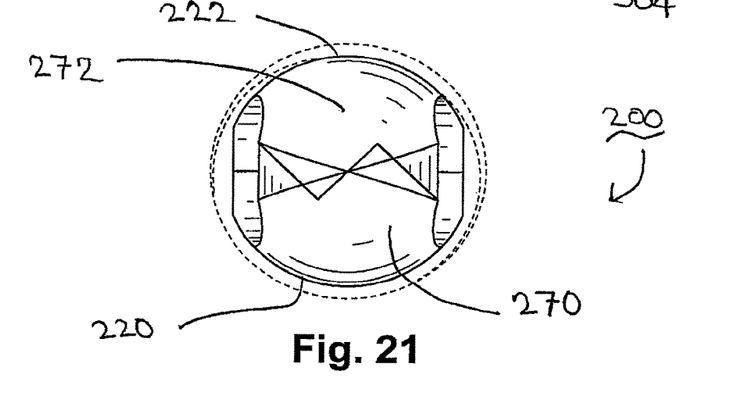
FIG. 21 is a front view of the distal end of the endoscopic grasping device of FIG. 17, with the jaws of the device shown in a closed position.

As discussed, the jaws 220, 222 in a closed position form a smooth, atraumatic distal tip. For example, upper jaw 222 has a smooth and convex distal surface 274 as best shown in FIG. 23. In addition, each jaw along its length is also shaped to prohibit soft tissue injury during insertion and removal of the grasping device from the patient. As seen in FIG. 19, the jaws in a closed position are torpedo shaped. The smooth outside surface 402 of the length of the jaws further prohibits soft tissue injury during insertion and removal of the grasping device from the patient.

A method of operation of the endoscopic grasping device as described herein is also inherent to the present invention.

While various inventive aspects, concepts, and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts, and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some aspects, concepts, and features of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, concepts, and features may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A device for use with an endoscope, the device comprising: a fork; and
   two jaws pivotally mounted about a pivot point of the fork, and movable between a predetermined closed position and a predetermined open position;
   wherein each jaw comprises front teeth near a distal end of the jaw and rear teeth near a proximal end of the jaw, wherein the front teeth of both jaws are configured to substantially mesh with each other when the jaws are in the closed position,
   wherein the substantially meshed front teeth of both jaws in the closed position form a substantially hemisphere-shaped distal tip and an object capture area proximal to curved portions of the front teeth,
   wherein at least a part of the proximal object capture area is defined by a distal side of one or more of the rear teeth being angled toward the proximal end of the jaw and a proximal side of the angled one or more rear teeth being substantially vertical to a centerline of the device when the jaws are in the closed position,
   wherein at least one of the two jaws includes a cupped portion formed between a row of teeth on a right side and a row of teeth on a left side of the jaw and wherein the rear teeth and the front teeth are disposed substantially around the cupped portion, and wherein at least one of the jaws has a length from its pivot point extending in a proximal direction that is at least about 33% of a length from its pivot point extending in a distal direction.

2. The device of claim 1 wherein the distal tip has an atraumatic surface.

3. The device of claim 1 wherein an interior surface formed by the substantially meshed front teeth of both jaws is substantially flat and substantially vertical to the centerline of the device.

4. The device of claim 1 wherein the front teeth of at least one of the two jaws extend across the centerline of the device.

5. The device of claim 4 wherein the front teeth of both jaws extend across the centerline of the device and wherein the meshed front teeth form a zigzag pattern.

6. The device of claim 1 wherein the front teeth of at least one of the two jaws are longer than the rear teeth of the same jaw.

7. The device of claim 6 wherein the front teeth of both jaws are longer than the rear teeth of the same jaw.

8. The device of claim 1 wherein the rear teeth of one of the two jaws are contiguous with the rear teeth of the other jaw along the centerline of the device.

9. The device of claim 1 wherein at least one rear tooth is pointed with essentially no radius.

10. The device of claim 1 wherein the object capture area is defined by curved jaw portions at a base of one or more of the front teeth or rear teeth.

11. A device for use with an endoscope, the device comprising:
    a fork; and
    a first jaw and a second jaw, the first jaw and the second jaw pivotally mounted about a pivot point of the fork and rotatable between a predetermined closed position and a predetermined open position;
    wherein each jaw comprises front teeth near a distal end of the jaw and rear teeth near a proximal end of the jaw,
    wherein the front teeth of both jaws are configured to substantially mesh with each other when the jaws are in the closed position,
    wherein the substantially meshed front teeth of both jaws in the closed position form a substantially hemisphere-shaped distal tip and an object capture area proximal to curved portions of the front teeth,
    wherein at least a part of the object capture areas is defined by a distal side of at least one rear teeth being angled toward the proximal end of the jaw,
    wherein at least one of the two jaws includes a cupped portion formed between a row of teeth on a right side and a row of teeth on a left side of the jaw and wherein the rear teeth and the front teeth are disposed substantially around the cupped portion, and
    wherein at least one of the jaws has a length from its pivot point extending in a proximal direction that is at least about 33% of a length from its pivot point extending in a distal direction.

12. The device of claim 11 wherein an interior surface formed by the substantially meshed front teeth of both jaws is substantially flat and substantially vertical to a centerline of the device.

13. The device of claim 11 wherein the front teeth of at least one of the two jaws extend across a centerline of the device.

14. The device of claim 13 wherein the front teeth of both jaws extend across the centerline of the device and wherein the meshed front teeth form a zigzag pattern.

15. The device of claim 11 wherein the front teeth of at least one of the two jaws are longer than the rear teeth of the same jaw.

16. The device of claim 15 wherein the front teeth of both jaws are longer than the rear teeth of the same jaw.

17. The device of claim 11 wherein the rear teeth of one of the two jaws are contiguous with the rear teeth of the other jaw along a centerline of the device.

18. The device of claim 11 wherein at least one rear tooth is pointed with essentially no radius.

19. A device for use with an endoscope, the device comprising:
- a body;
- a handle mounted to and movable relative to the body;
- a conduit having a first end fixed to the body and a second end, the conduit defining a passage and an opening at the second end;
- a fork having two prongs and attached to a distal end of the conduit;
- a first jaw and a second jaw, pivotally mounted about a pivot point of the fork within the two prongs, and dependently movable between a predetermined closed position and a predetermined open position; and
- wherein each jaw comprises front teeth near a distal end of the jaw and rear teeth near a proximal end of the jaw,
- wherein the front teeth of both jaws are configured to substantially mesh with each other when the jaws are in the closed position,
- wherein the substantially meshed front teeth of both jaws in the closed position form a substantially hemisphere-shaped distal tip and an object capture area proximal to curved portions of the front teeth,
- wherein at least a part of the object capture area is defined by a distal side of at least one rear teeth being angled toward the proximal end of the jaw and a proximal side of a neighboring tooth to the angled at least one rear teeth being substantially vertical to a centerline of the device when the jaws are in the closed position, and
- wherein at least one of the first and second jaws includes a cupped portion formed between a row of teeth on a right side and a row of teeth on a left side of the jaw and wherein the rear teeth and the front teeth are disposed substantially around the cupped portion.

20. The device of claim 19 wherein the distal tip has an atraumatic surface.

21. The device of claim 19 wherein an interior surface formed by the substantially meshed front teeth of both jaws is substantially flat and substantially vertical to the centerline of the device.

22. The device of claim 19 wherein the front teeth of at least one of the two jaws extend across the centerline of the device.

23. The device of claim 22 wherein the front teeth of both jaws extend across the centerline of the device and wherein the meshed front teeth form a zigzag pattern.

24. The device of claim 19 wherein the object capture area is defined by curved jaw portions at a base of one or more of the front teeth or rear teeth.

* * * * *